United States Patent
Nchekwube et al.

(10) Patent No.: US 9,877,487 B2
(45) Date of Patent: Jan. 30, 2018

(54) COMPOSITIONS FOR EFFECTIVE FLY POPULATION SUPPRESSION

(71) Applicant: EMEKATECH, LLC, Santa Clara, CA (US)

(72) Inventors: Emeka J. Nchekwube, Morgan Hill, CA (US); Cyprian Emeka Uzoh, San Jose, CA (US)

(73) Assignee: EMEKATECH, LLC, Santa Clara, CA (US)

( * ) Notice: Subject to any disclaimer, the term of this patent is extended or adjusted under 35 U.S.C. 154(b) by 0 days.

(21) Appl. No.: 14/906,529

(22) PCT Filed: Jul. 17, 2014

(86) PCT No.: PCT/US2014/047105
§ 371 (c)(1),
(2) Date: Jan. 20, 2016

(87) PCT Pub. No.: WO2015/013110
PCT Pub. Date: Jan. 29, 2015

(65) Prior Publication Data
US 2016/0157496 A1 Jun. 9, 2016

Related U.S. Application Data

(60) Provisional application No. 61/961,949, filed on Oct. 28, 2013, provisional application No. 61/958,241, filed on Jul. 22, 2013.

(51) Int. Cl.
| | |
|---|---|
| *A01N 63/02* | (2006.01) |
| *A01N 63/04* | (2006.01) |
| *A01M 1/02* | (2006.01) |
| *A01N 25/00* | (2006.01) |
| *A01N 25/34* | (2006.01) |
| *A01M 1/10* | (2006.01) |
| *A01M 1/04* | (2006.01) |
| *A01M 1/20* | (2006.01) |

(52) U.S. Cl.
CPC ............. *A01N 63/02* (2013.01); *A01M 1/02* (2013.01); *A01M 1/04* (2013.01); *A01M 1/106* (2013.01); *A01M 1/2016* (2013.01); *A01N 25/006* (2013.01); *A01N 25/34* (2013.01)

(58) Field of Classification Search
None
See application file for complete search history.

(56) References Cited

U.S. PATENT DOCUMENTS

| | | | |
|---|---|---|---|
| 1,238,539 A | 8/1917 | Joseph | |
| 2,645,877 A | 7/1953 | Pohlman | |
| 2,715,295 A | 8/1955 | Brown | |
| 2,979,856 A | 4/1961 | Ponting | |
| 3,420,933 A | 1/1969 | Helmuth et al. | |
| 3,846,557 A * | 11/1974 | Mulla | A01N 25/006 426/1 |
| 4,037,351 A | 7/1977 | Springer | |
| 4,638,592 A | 1/1987 | Schneidmiller | |
| 4,685,868 A | 8/1987 | Bodensteiner et al. | |
| 4,718,193 A | 1/1988 | Rosselli | |
| 4,849,216 A * | 7/1989 | Andersen | A01N 25/006 424/84 |
| 4,855,133 A * | 8/1989 | Kamei | A01N 25/006 424/84 |
| 5,124,149 A * | 6/1992 | Shapiro | A01N 63/00 424/405 |
| 5,126,139 A | 6/1992 | Geary | |
| 5,142,817 A | 9/1992 | Rolf | |
| 5,466,459 A | 11/1995 | Wilson | |
| 5,713,788 A * | 2/1998 | Ferket | A22B 7/008 241/15 |
| 5,800,897 A | 9/1998 | Sharma et al. | |
| 5,951,946 A | 9/1999 | Eaton et al. | |
| 6,231,865 B1 | 5/2001 | Hsu et al. | |
| 7,074,830 B2 | 7/2006 | Durand et al. | |
| 8,772,348 B2 | 7/2014 | Kaufman et al. | |
| 2003/0040504 A1 | 2/2003 | Gans et al. | |
| 2004/0001870 A1* | 1/2004 | Durand | A01M 1/02 424/405 |

(Continued)

FOREIGN PATENT DOCUMENTS

| | | |
|---|---|---|
| BR | PI0902057 A2 | 1/2010 |
| CA | 2057008 A1 | 11/1990 |

(Continued)

OTHER PUBLICATIONS

A webpage from www.olympusmicro.com [retrieved on Jul. 19, 2016]. Retrieved from the Internet: <URL: http://www.olympusmicro.com/primer/techniques/fluorescence/fluorotable2.html>, Mar. 9, 2002.*

Olympusmicro, a webpage at www.olympusmicro.com [retrieved on Mar. 17, 2017]. Retrieved from the Internet: <URL:http://www.olympusmicro.com/primer/techniques/fluorescence/fluorotable2.html>.*

Biernacki, AE., Identifying the Signature of the Natural Attenuation of MTBE in Groundwater using Molecular Methods and Bug Traps. Master's Thesis, University of Tennessee, 2004. Retrieved on Oct. 24, 2016. Available at http://trace.tennessee.edu/utk_gradthes/1871.

Co-pending U.S. Appl. No. 15/119,830, filed Aug. 18, 2016.

(Continued)

*Primary Examiner* — Robert T. Crow
*Assistant Examiner* — John P Nguyen
(74) *Attorney, Agent, or Firm* — Wilson Sonsini Goodrich & Rosati

(57) ABSTRACT

Provided herein are systems, devices, methods, and compositions for suppressing a population of certain species of insects such as flies. Compositions comprising an anaerobically fermented biomass, a dye and a particulate matter, are disclosed, some of which are selective in attracting a harmful insect, and are biodegradable, non-toxic and environmentally friendly. Systems and methods for use of the compositions are described herein.

19 Claims, 24 Drawing Sheets

(56) References Cited

U.S. PATENT DOCUMENTS

| | | |
|---|---|---|
| 2004/0025412 A1 | 2/2004 | Simchoni et al. |
| 2004/0057977 A1 | 3/2004 | Gardner et al. |
| 2004/0208953 A1 | 10/2004 | Heath |
| 2005/0008531 A1 | 1/2005 | Parkhurst et al. |
| 2005/0169955 A1* | 8/2005 | Simchoni Barak .... A01N 59/04 424/410 |
| 2006/0150473 A1 | 7/2006 | Bette et al. |
| 2006/0260183 A1 | 11/2006 | Hockaday |
| 2007/0011940 A1 | 1/2007 | Chen et al. |
| 2010/0003198 A1 | 1/2010 | Stolmeier et al. |
| 2010/0112105 A1 | 5/2010 | Hoyt et al. |
| 2011/0158934 A1* | 6/2011 | Nishiguchi .......... A01N 25/006 424/84 |
| 2014/0020694 A1 | 1/2014 | Moldoveanu et al. |

FOREIGN PATENT DOCUMENTS

| | | |
|---|---|---|
| CN | 101885541 A | 11/2010 |
| CN | 102106356 A | 6/2011 |
| CN | 202354254 U | 8/2012 |
| CN | 103210960 A | 7/2013 |
| CN | 103704282 A | 4/2014 |
| ES | 2288378 A1 | 1/2008 |
| FR | 2614507 A1 | 11/1988 |
| JP | 2012044885 A | 3/2012 |
| WO | WO-91/05833 | 5/1991 |
| WO | WO-96028749 | 9/1996 |
| WO | WO-2010117191 A2 | 10/2010 |
| WO | WO-2010126794 A1 | 11/2010 |
| WO | WO-2012033422 A1 | 3/2012 |
| WO | WO-2014053406 A1 | 4/2014 |
| WO | WO-2015013110 A1 | 1/2015 |
| WO | WO-2015127311 A1 | 8/2015 |
| WO | WO-2016115539 A1 | 7/2016 |

OTHER PUBLICATIONS

Dealbuquerque, TA., Diversity and Effect of the Microbial Community of Aging Horse Manure on Stable Fly (Stomoxys calcitrans) Fitness. Department of Entomology: College of Agriculture. Kansas. 2012; pp. 1-120: Retrieved on Oct. 24, 2016; Available at http://krex.k-state.edu/dspace/bitstream/handle/2097/14191/ThaisAibuquerque20 12.pdf.

International Search Report and Written Opinion dated Apr. 4, 2016 for International Application PCT/US2016/013727.

International search report and written opinion dated Dec. 16, 2014 for PCT/US2014/047105.

International Search Report dated Jul. 16, 2015 for International Application PCT/US2015/016964.

Zurek, et al., Diversity and contribution of the intestinal bacterial community to the development of *Musca domestica* (Diptera: Muscidae) larvae. J Med Entomol. Nov. 2000;37(6):924-8.

European search report with written opinion dated Feb. 28, 2017 for EP14829663.

* cited by examiner

Embodiment displaying field deployment of invention in a shade magnified view

Effects of bath formulation on fly trapping efficiency – After 60 minutes

F2: (F1 + Fluorescent Dye A)

F1: (Control Effluent, 2L)
Water
Squid 0.1 to 10lb/5gal
Carbon dioxide – 0.1 to 5lb
Clay 0.1 to 10g Effects of bath formulation on fly trapping efficiency – After 3days

F1

F2

Effects of bath formulation on fly trapping efficiency – After 6 days

Attractant C = Water (Control)

F1  F2

Evidence for effectiveness of fly clustering:
A – Formulation from ground aquatic biomass
B - formulation from effluent (without grinding the biomass)
C – Formulation with excess dye.

Water in bottle for control

Effect of Dye

Maggots

Fermented ground aquatic biomass

COMPOSITIONS FOR EFFECTIVE FLY POPULATION SUPPRESSION

CROSS-REFERENCE

This application claims the benefit to U.S. Provisional Application No. 61/958,241, filed on Jul. 22, 2013, which is hereby incorporated by reference in its entirety, U.S. Provisional Application No. 61/961,949, filed on Oct. 28, 2013, which is hereby incorporated by reference in its entirety, and Patent Application No. PCT/US2014/047105, filed Jul. 17, 2014, which is hereby incorporated by reference in its entirety.

INCORPORATION BY REFERENCE

All publications, patents, and patent applications mentioned in this specification are herein incorporated by reference to the same extent as if each individual publication, patent, or patent application was specifically and individually indicated to be incorporated by reference.

FIELD OF THE INVENTION

The invention relates to the suppression of populations of certain insect species such as flies.

BACKGROUND OF THE INVENTION

The house fly, horse fly and other members of their family are not only a nuisance, they are pests at both homes and farms, and often they are laden with disease causing organisms. In developed countries, typically flies are the most common species found on hog and poultry farms, dairy farms, horse stables and ranches where they are associated with feces and garbage. In developing countries, with poor public hygiene and sanitation that is elementary or less than elementary, the accompanying undesirable very high fly population is a serious public health problem. Fly induced stress and illness is a major source of revenue and energy drain for industrial animal farming operations and the public sector.

Many good efforts have been made to suppress fly population in urban and farm settings. Apart from improved public and private sanitation, keeping windows screened and doors closed, sticky traps (fly paper) and ultraviolet light traps (non-chemical control) placed around a home or business also can reduce housefly populations. They normally function by electrocuting flies that enter the trap.

In industrial farming operations, for example in commercial egg production facilities, flies densities may be suppressed by the application of insecticides (adulticides or larvacides) directly or indirectly to where the flies congregate or their favorite resting locations. However, resistance to commonly used insecticides is increasingly problematic. For example, fly populations that are subjected to a continuous permethrin regime on industrial farms have rapidly developed resistance to permethrin. Treating manure with insecticide, though this method is highly discouraged as it interferes with biological control of flies, often results in a rebound of the fly population. In some cattle and horse ranches, insecticides (especially insect growth regulators) are fed to livestock, and residual insecticide in the manure inhibits fly breeding. Continuous exposure of flies to insecticides has led to development of resistance to many insecticides.

Chemical control suppression of the fly population has been partially effective and there exists a need for a new method or system to effectively suppress the fly population. This new method should be accomplished in a manner that does not result in insecticide resistance. There is a need for a method that is ecologically not toxic.

SUMMARY OF THE INVENTION

Provided herein is a device comprising: a) a partially enclosed hollow container, comprising an orifice sufficiently large to allow said insect to enter the container; and b) an insect attractant layer comprising an insect attractant deposited within said container; wherein the container is configured to capture and kill the insect such that the killed insect is deposited above or within the insect attractant layer, and further wherein the insect attractant layer comprises an aquatic biomass material. In some embodiments, each of the one or more species of insect is within the subclass Pterygota, for example a fly. In some embodiments, each of the one or more species of insect are selected from the group consisting of black flies, cluster flies, crane flies, deer flies, face flies, flesh flies, green flies, horn flies, horse flies, house flies, sand flies, sparaerocierid flies, yellow flies, western cherry fruit flies, tsetse flies, cecid flies, phorid flies, sciarid flies, stable flies, mites, and gnats. In some embodiments, the attractant is an effluent. In some embodiments, the killed insects form a layer deposited within the attractant. In some embodiments, the attractant further comprises terrestrial biomass material. In some embodiments, the aquatic biomass is selected from the group consisting of cuttlefish, mussel, octopus, squid, clam, oyster, scallop, mussel, snail, and slug. For example, the aquatic biomass can be comprised of aquatic flotsam, fish waste, or aquatic waste. In some cases, the attractant comprises plant-derived biomass. In some embodiments, at least a portion of the attractant has been fermented. In some embodiments, the fermentation reaction is substantially anaerobic. In some embodiments, the fermentation reaction comprises yeast. In some embodiments, the fermentation reaction comprises the addition of $CO_2$.

In some embodiments of the device provided herein, the attractant further comprises a dye, for example, an edible dye or parenteral dye, or a biodegradable dye. In some embodiments, the dye is a fluorescent dye with an emission wavelength between 200 and 600 nm, for example between 300 and 450 nm. In some embodiments, the attractant comprises between 0.01 ppm and 1000 ppm dye on a dry matter basis (wt/wt).

In some embodiments of the device provided herein, the attractant further comprises particulate matter, for example, nanoparticles and/or particulate matter with size varying between 0.5 nm to 12 cm. In some embodiments, the particulate matter is selected from the group consisting of polymer clay, Edgar plastic kaolin, silicon powders, carbon particulates, activated carbon, volcanic ash, kaolinitic clays, montmorillonite, and treated saw dust. In some embodiments, the particulate matter is kaolinite, montmorillonite, silicon dioxide or treated saw dust. In some cases, the device comprises less than 5% particulate matter (wt/wt).

In some embodiments of the device described herein, the attractant is derived from an attractant precursor, wherein the attractant precursor is dehydrated or freeze-dried. In some cases, the liquid is water. In some embodiments, the attractant does not comprise a synthetic insecticide. In other embodiments, the attractant contains a maggocide. In some embodiments, the device further comprises a plurality of trapped insects; wherein the plurality of trapped insects form an insect layer. In some embodiments, the insect layer is thick enough to form a substantially anaerobic seal over the attractant layer. In some cases, the attractant permeates the insect layer. In some embodiments, the insect layer is at least 8, 24, 28, or 30 cm thick. In some embodiments, the device is configured to prevent the detectable growth of maggots in the device.

In some embodiments of the device described herein, the device further comprises a pulsing or non-pulsing light emitting diode. In some embodiments, the container is configured to hold at least 100, 200, 300, 400, 500, 600, 700, 800, 900, 1000 or 6000 mL of attractant. In some embodiments, the container is configured to hold less than 10000, 7000, 5000, or 4000 mL of attractant. In some cases, the container is transparent or translucent. In some embodiments, the container is coated with paint. In some embodiments, the paint is an infra-red reflecting paint. IN some embodiments, the container is coated with an infra-red absorbing layer.

In some embodiments, the device comprises a plurality of orifices; wherein each orifice is sufficiently large to permit the entrance of the insect; and wherein each of the orifices provides air or fluid communication between the inside of the container and the outside environment. In some embodiments, there is no direct line of sight between any two orifices. In some embodiments, the side of the container comprises at least 1, 2, 3, 4, or 5 non-vertical ledges. In some embodiments, each of the non-vertical ledges is perpendicular to the side of the container. In some embodiments, each of the non-vertical ledges slopes downward. In some embodiments, the container comprises a lid. In some embodiments, the lid is coated with infra-red absorbing layer. In some embodiments, the orifice is positioned between the lid and the container. In some embodiments, the orifice is an opening surround by a substantially concave surface. In some embodiments, the orifice is an opening surround by a substantially convex surface. In some embodiments, the orifice is a tunnel. In some embodiments, the lid is substantially opaque. In some embodiments, the lid is coated with a thermally reflective material. In some embodiments, the device further comprises an opaque cover positioned above said container. In some embodiments, the cover is coated with a thermally reflective material.

In another aspect, provided herein is an array of insect traps comprising a plurality of insect traps positioned in proximity to each other, wherein the array comprises at least two traps cluster in an area of less than 100 square feet. In some embodiments, said traps are present in an area of less than 50, 30, 20, 10 square feet. In some embodiments, the array comprises at least 3, 4, 5, 6, 7, 8, 9, or 10 insect traps. In some embodiments, the array is capable of suppressing the population of one or more species of insect of an area greater than 0.1, 0.3, 0.5, 0.7, 1.0, 1.5, 2.0, 3.0, 5.0, 7.0 or 10 acres. In some embodiments of the array, the one or more species are selected from the group consisting of black flies, cluster flies, crane flies, deer flies, face flies, flesh flies, green flies, horn flies, horse flies, house flies, sand flies, sparaerocierid flies, yellow flies, western cherry fruit flies, tsetse flies, cecid flies, phorid flies, sciarid flies, stable flies, mites, and gnats. In some embodiments, each insect trap comprises a chemical attractant. In some embodiments, each insect trap comprises a volume of attractant of at least 100, 200, 300, 400, 500, 600, 700, 800, 900, or 1000 mL. In some embodiments, each trap is configured to capture and kill the insect such that the killed insect is deposited above or with the insect attractant layer. In some embodiments, each insect trap is a device described herein.

In another aspect, provided herein is a composition comprising processed biomass, a fluorescent dye, and particulate matter. In some embodiments, the biomass is processed by a physical processing step selected from the group consisting of cutting, chopping, grinding, or milling. In some embodiments, the processed biomass is present as fine particulates or semi-solid. In some embodiments, a first portion of the processed biomass is sterilized. In some embodiments, a first portion of the processed biomass is pasteurized. In some embodiments, a first portion of the processed biomass is treated with UV light. In some embodiments, a second portion of the processed biomass is fermented. In some embodiments, the processed biomass is aquatic biomass, terrestrial biomass, or a combination thereof. In some embodiments, the processed biomass comprises aquatic biomass. In some embodiments, the processed biomass comprises fish waste or aquatic waste. In some embodiments, the aquatic biomass is selected from the group consisting of cuttlefish, mussel, octopus, squid, clam, oyster, scallop, snail, slug and the combination thereof. In some embodiments, the dye is a fluorescent dye with an emission wavelength between 200 and 600 nm. In some embodiments, the composition comprises between 0.1 ppm and 20,000 ppm dye on a dry matter basis (wt/wt). In some embodiments, the particulate matter is selected from the group consisting of ball clay, bentonite clay, polymer clay, Edgar plastic kaolin, silicon powders, carbon particulates, activated carbon, volcanic ash, kaolinitic clays, montmorillonite, and treated saw dust, for example, the particulate matter is montmorillonite or treated saw dust. In some embodiments of the compositions provided herein, the pH is between about 3 and 9, for example, the pH is between about 5 and 8. In some embodiments the composition further comprises a resinous material; for example, guar or xanthan gum.

In some embodiments of the device provided herein, the insect attractant layer is at least 30, 40, or 50 liters. In some embodiments, the device is configured to be at least partially underground. In some embodiments, the device comprises a port configured to be reversibly attached to a vacuum, wherein application of a vacuum to the port results in the removal of a portion of the contents of the trap. In some embodiments, the portion of contents is at least 40, 50, 60, 70, 80, 90, 95, or 99% of the contents of the trap.

Further provided herein, is a method of suppressing a population of one or more species of insect in a defined area, wherein the method comprises: deploying the device provided herein. Also provided is a method of suppressing a population of one or more species of insect in a defined area, wherein the method comprises: deploying the array provided herein. In some embodiments of the method provided herein, the defined area is at least 0.1, 0.2, 0.3, 0.4, 0.5, 1, 2, 3, or 4 acres. In some embodiments, suppressing of the population is determined by the number of insects captured or killed 6 days after deployment of the trap or the array; and wherein the number of insects captured or killed is at least 3000, 5000, 10000, 20000, or 50000 insects. In some embodiments, fewer than 0.5% of insects that enter the container exit the container. In some embodiments, the one or more species of insect is within the subclass Pterygota, for example a fly. In some embodiments, each of the one or more species of insect are selected from the group consisting of black flies, cluster flies, crane flies, deer flies, face flies, flesh flies, green flies, horn flies, horse flies, house flies, sand flies, sparaerocierid flies, yellow flies, western cherry fruit flies, tsetse flies, cecid flies, phorid flies, sciarid flies, stable flies, mites, and gnats. In some embodiments, grasshopper, bees, and butterfly populations are not suppressed. Further provided is a fertilizer comprising the captured flies described herein. In some embodiments, the fertilizer further comprises ammonium nitrate.

In another aspect, provided herein is a method for the production of flies or maggots, the method comprising deploying the device provided herein, wherein the device is configured to allow the growth of maggots. Also provided, is a method for the production of flies or maggots, the method comprising deploying the array described herein, wherein the device is configured to allow the growth of maggots. In some embodiments of the methods, the device comprises the composition described herein.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
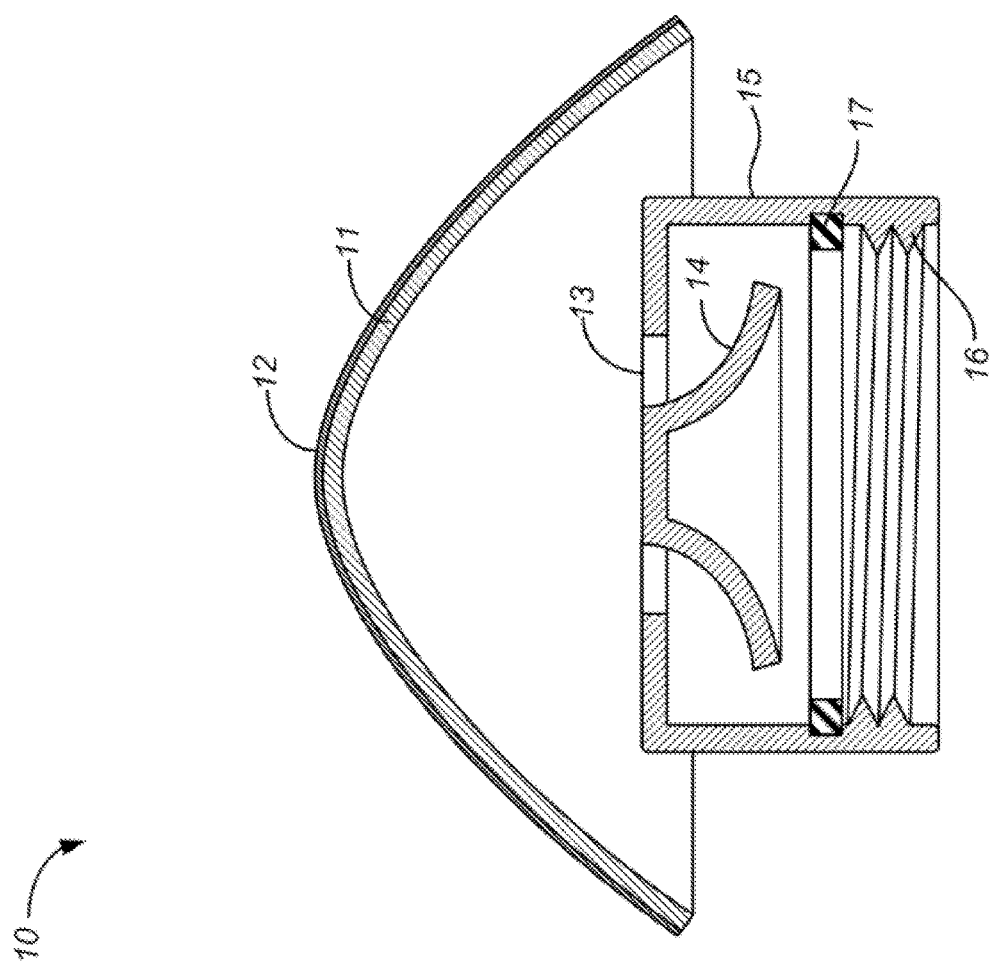
FIG. 1 depicts a cross section of container lid or cap with canopy coated with thermal paint.

Disclosed herein is a highly effective and efficient system for suppression of varies species of insects. In some embodiments, the system is effective for suppression of one or more species of insects within the insect subclass Pterygota. Pterygota includes the winged insects and insect orders that are secondarily wingless (that is, insect groups whose ancestors once had wings but that have lost them as a result of subsequent evolution). In some embodiments, the device and methods described herein are configured to effectively attract, kill, or suppress one or more species of true flies or flies of the order Diptera. In some embodiments, the systems and methods described herein are effective for attracting, trapping, killing, or suppressing populations of flies selected from the group consisting of black flies, cluster flies, crane flies, deer flies, face flies, flesh flies, green flies, horn flies, horse flies, house flies, sand flies, sparaerocierid flies, yellow flies, western cherry fruit flies, tsetse flies, cecid flies, phorid flies, sciarid flies, stable flies, mites, and gnats. In some embodiments, the system or method is effective for suppression of house and horse flies. In some embodiments, the attractant may be modified to trap tsetse fly. In some embodiments, the system and methods are effective for suppression of tiny insects including mosquitoes.

Systems and methods described herein can exhibit selectivity in attracting, killing, or suppressing an insect population of one or more insect species. The selectivity can be gender selectivity. In some embodiments, the systems and methods described herein effectively attract both males and females of one or more insect species. In some cases, the attractant of this invention has a very high affinity for the females of a species. In some cases, the attractant of this invention has a very high affinity for the females of a species. The selectivity can be species selectivity. In some embodiments, the system or methods described herein are configured to more effectively attract, kill or suppress the population of one or more first insect species to a greater degree than one or more second insect species. For example, the system or methods disclosed herein can be effective for selectively suppressing a population of house flies and/or horse flies while not suppressing the population of a second insect species. In some embodiments, the second insect species is an *Apis*. In some embodiments, the second species is selected from the group consisting of grasshopper, bee (ie honeybee) and butterfly.

Deployment of a system or device disclosed herein, or use of a method disclosed herein can suppress an insect population in a specified environment. Non-limiting examples of environments which can exhibit suppressed insect populations of one or more insect species include farmland, horse pastures, poultry pastures, grazing and non-grazing livestock ranch, slaughterhouses, meat and fish processors, dairy farms, hog farms, beaches, restaurants, homes, boats, recreational park areas, produce farms, hospitals, landfills, mushroom farms, waste management facilities, or composting.

The insect trap apparatus as described herein comprises a container which holds the attractant. In some cases, the trap further comprises one or two additional parts, wherein the additional parts are selected from a lid and a modified cover. The attractant, container, optional lid, and modified cover are each described in further detail herein.

Figure 2:
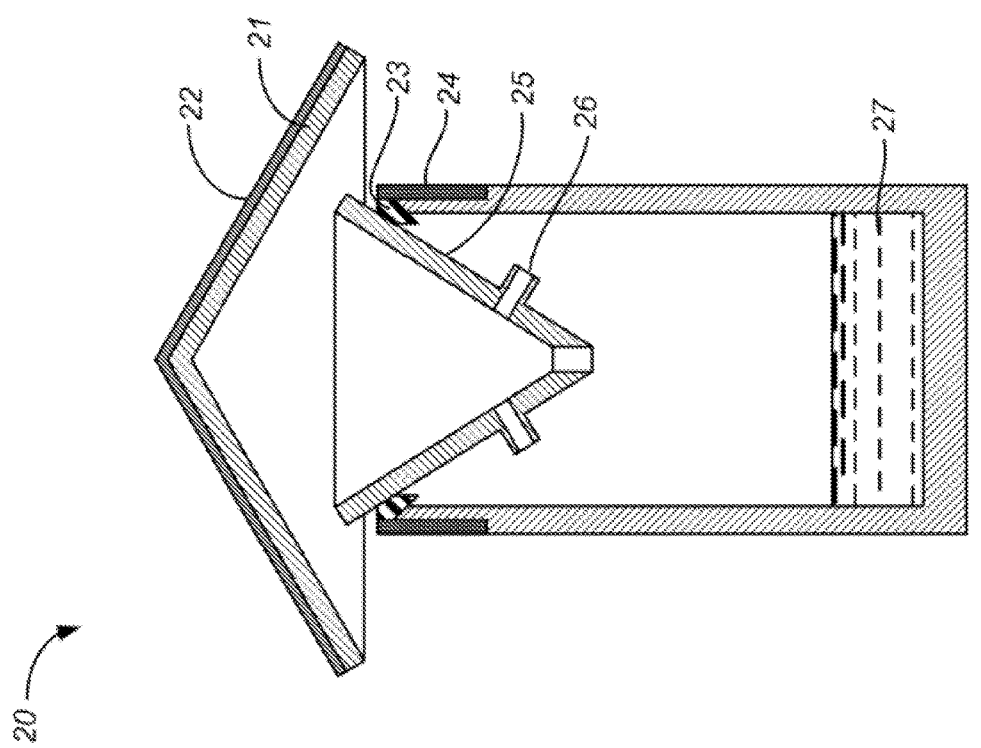
FIG. 2 depicts a fly trap with modified funnel top comprising trap shade coated with thermal paint.

In some non-limiting embodiments, the apparatus (20) is configured as in FIG. 2. In some embodiments, the container is covered by a lid or shade (21) which is optionally coated with thermal paint (22). The lid can be attached to the container by a seal structure (23) which is optionally coated with an opaque coating (24). In some embodiments, a modified funnel (25) rests above the container but below the trap shade. The modified funnel comprises one or more apertures for fly entrance (26). In some embodiments, the container holds the attractant (27).

In some non-limiting embodiments, the apparatus (30) is configured as in FIG. 2. In some embodiments, the container is covered by a lid or shade (31) which is optionally coated with thermal paint (32). The lid can be attached to the container by a seal structure (33). In some embodiments, the top of the container comprises one or more orifices (34) for small insects. In some embodiments, a modified funnel (35) rests above the container but below the trap shade. The modified funnel comprises one or more apertures for fly entrance (36). In some embodiments, the container holds the attractant (37).

In some embodiments, the apparatus (10) comprises a lid configured according to FIG. 1. In some embodiments of the lid, a canopy (11) rests above the lid. In some embodiments, the canopy is coated with thermal paint (12). In some embodiments, the top of the lid below the canopy comprises one or more apertures for fly entrance (13). In some embodiments, a convex/concave structure (14) is disposed directly below the aperture. The outside of the lid (15) can be clear or opaque. In some embodiments, the cap attaches to the container below it via a screw mechanism, for example by screwing a cap thread structure (16). In some embodiments, a seal structure (17) is disposed above the cap thread.

One unique aspect of this invention is the observation that the incorporation of particulate materials and some dyes in the attractant material suppresses the emergence of maggots from the trapped flies in the deployed traps. The suppression of fly egg development/elimination of maggots reduces the risk of insect resistance to the attractants of this invention. The attractant may be deployed in container with modified cover and the various flies of interest enter the container and are overwhelmed by the attractant and exhibit no inclination to escape from the said container. The attracted flies may die from drowning, starvation, hypoxia, or from compounds emanating from the attractant or from unknown causes. Because no fly escapes from the said attractant container, the incidence of resistance is remote and less likely.

The methods, devices, or systems described herein, each comprise an attractant. The attractant is a composition that attracts one or more species of insects. Additional examples of attributes that make a composition an acceptable attractant can include specificity in attracting only desired insect species, ability to be synthesized inexpensively from organic materials, very low toxicity to humans and animals (horse, cattle birds, chicken etc.) when deployed, and low environmental toxicity of the waste products after deployment. In some embodiments, the organically formulated attractant does not contain synthetic pesticides. Use of an attractant composition with low environmental toxicity can enable the waste material after deployment to be compostable used as a fertilizer, food for an animal such as a bird or fish.

In some embodiments, the attractant composition comprises an attractant precursor composition, a dye, and optionally a particulate additive.

In some embodiments, the attractant precursor composition comprises biomass material. The attractant composition can comprise biomass materials from one or more animal sources, plants sources, or a combination thereof. The biomass from an animal source or plant source can be aquatic biomass, terrestrial biomass, or a combination thereof. The biomass can be industrial or non-industrial biomass. In some embodiments, to reduce cost and/or improve effectiveness, the biomass material used to synthesize the attractant can be biomass waste. The biomass waste may comprise of visceral or somatic parts or excretions, including manure.

The attractant can comprise biomass from an animal source. For example, animal biomass can include terrestrial biomass such as slaughterhouse waste, food and non-food wastes, poultry processing plant wastes, swine processing wastes, dead stock, spoiled meat, and spoiled poultry. The fish biomass can include marine animals, freshwater animals, fish flotsam, vertebrates, invertebrates, or any combination thereof. In some embodiments, mollusks such as cephalopods, gastropoda, bivalvia species may be used as the precursor material. For example, cuttlefish, mussels, octopus, squids, may be used alone or combined with clams, oysters, scallops, mussel, snails, slug and their likes for precursor material. In other embodiment, marine water biomass or fresh water biomass may be used alone or in combination. In one embodiment, terrestrial biomass waste may be combined with fresh water or marine biomass or aquatic flotsam for precursor material.

In some embodiments, terrestrial and aquatic plants may be used for precursor material. In one example terrestrial plants such castor oil seed may be boiled and fermented as an attractant. The fermented and unfermented seeds may be combined in appropriate proportions. In another example aquatic plants such as kelp may be fermented as an attractant for this invention. The fermented and unfermented plant may be combined in appropriate proportions as the precursor material or as attractant material. In one embodiment, terrestrial or aquatic biomass may be applied as precursor or as attractant for this invention. In some applications, materials from plant and animal sources may be combined and applied as a precursor or as attractant for this invention.

In some embodiments, the attractant comprises one or more dyes. An effective dye can emit light that increases the attraction of insects, is relatively inexpensive, exhibits low toxicity to humans and animals while deployed, and is safely disposed of after deployment. In some cases, the attractant may comprise a single dye. Alternatively, the attractant can comprise multiple dyes. In some embodiments, the attractant comprises a fluorophore or fluorescent dye. In some embodiments the dye comprises edible dyes, injectable dyes, parenthral dyes, or nontoxic dyes and preferably biodegradable dyes. The fluorescent dye may be hydrophilic or hydrophobic in nature. The attractant may comprise one or more fluorescing ultra-violet dyes, or dyes that fluoresce within visible or non-visible spectrum of light. The dye may be added to the precursor material prior to the fermentation step. More may be added if desirable. In some applications, the dye may be incorporated into the attractant post fermentation.

In some embodiments, the dye is selected from the group consisting of acridine dyes, cyanine dyes, fluorone dyes, oxazin dyes, phenanthridine dyes, and rhodamine dyes. In some embodiments, the dye is selected from the group consisting of acridine orange, acridine yellow, ALEXAFLUOR (Molecular Probes, Inc.), AUTOPRO 375 Antifreeze/Coolant UV Dye 1 (Autopro Parts Professionals), benzanthrone, bimane, bisbenzimidine, blacklight paint, brainbow, calcein, carboxyfluorescein, coumarin, DAPI (Thermo Fisher Scientific), DYLIGHT Fluor (Dyomics and Thermo Fisher Scientific), Dark quencher, Epicocconone, ethidium bromide, Fluo, Fluorescein, Fura, GELGREEN (Biotium), GELRED (Biotium), Green fluorescent protein, heptamethine dyes, Hoechst stain, Iminocoumarin, Indian yellow, Indo-1, Laurdan, Lucifer yellow, Luciferin, MCherry, Merocyanine, Nile blue, Nile red, Perylene, Phioxine, Phycobilin, Phycoerythrin, Pyranine, Propidium iodide, Rhodamine, RIBOGREEN (Molecular Probes/Invitrogen), RoGFP, Rubrene, Stilbene, Sulforhodamine, SYBR dyes (Thermo Fisher Scientific), tetraphenyl butadiene, Texas red, Titan yellow, TSQ, Umbelliferone, Violanthrone, Yellow fluorescent protein, and YOYO.

In some embodiments, the attractant comprises an amount of one or more dyes less than 1.0%, 0.9%, 0.8%, 0.7%, 0.6%, 0.5%, 0.4%, 0.3%, 0.2%, 0.1%, 0.05%, 0.01%, 0.0001%, 0.00001%, 0.000001%, or 0.0000001% on a dry matter basis (wt/wt). In some embodiments, the attractant comprises an amount of one or more dyes greater than 1.0%, 0.9%, 0.8%, 0.7%, 0.6%, 0.5%, 0.4%, 0.3%, 0.2%, 0.1%, 0.05%, 0.01%, 0.0001%, 0.00001%, 0.000001%, or 0.0000001% on a dry matter basis (wt/wt). In some embodiments, the attractant comprises an amount of one or more dyes less than 5% but greater than 1.0%, 0.9%, 0.8%, 0.7%, 0.6%, 0.5%, 0.4%, 0.3%, 0.2%, 0.1%, 0.05%, 0.01%, 0.0001%, 0.00001%, 0.000001%, or 0.0000001% on a dry matter basis (wt/wt). In some embodiments, the attractant comprises between 0.01 ppm and 1,000 ppm of one or more dye.

In some embodiments, the attractant comprises a dye having an emission wave length less than 800, 750, 700, 650, 640, 630, 620, 610, 600, 590, 580, 570, 560, 550, 500, 450, 400, 350, 300, 250, 200, or 150 nm. In some embodiments, the attractant comprises a dye having an emission wave length greater than 150, 200, 250, 260, 270, 280, 290, 300, 310, 320, 330, 340, 350, 400, 450, 500, 550, 600, 650, 700, 750, or 800 nm. In some embodiments, the attractant comprises a dye having an emission wavelength between 200 and 700 nm, 250 and 650 nm, or between 300 and 600 nm. In some embodiments, the attractant comprises a dye with an emission wavelength between 300 and 600 nm. In some embodiments, the attractant comprises a dye with an emission wavelength between 200 and 400 nm.

The attractant can comprise a particulate additive, a colloidal material, or a combination thereof. A particulate or colloidal material as an additive can stabilize the attractant composition and increase the shelf life. Additionally, it is observed that the incorporation of particulate materials in the attractant material may suppress the emergence of maggots from the trapped flies in the deployed traps. The suppression of fly egg development/elimination of maggots reduces the risk of insect resistance to the attractants of this invention. In some embodiments, the attractant comprises of one or more colloidal materials including particulates. In some embodiments, particulates or colloidal material may be added to the precursor material or formulated into the attractant post fermentation.

In some embodiments, the attractant comprises one or more particulate additives selected from the group consisting of polymer clay, ball clay, Edgar plastic kaolin, silicon powders, bentonite clay, carbon particulates, activated carbon, volcanic ash, kaolinitic clays, montmorillonite and treated saw dust. In some embodiments, the attractant comprises one or more particulate additives selected from the group consisting of montmorillonite, and treated saw dust. In some embodiments, the attractant comprises one or more carbohydrates or carbohydrate moieties such as glue, starch or gelatinized starch. The attractant of this invention may be formulated with colloidal materials to form an emulsion or semi-solid/liquid media. The combination of dead flies and the emulsion can form a semi-solid or sludge. The resulting semi-solid or sludge can be an efficient attractant, and further cause insects to come into the container.

In some embodiments, the attractant comprises an amount of particulate additives less than 90, 85, 80, 80, 75, 70, 65, 60, 55, 50, 45, 40, 35, 30, 25, 20, 15, 10, 5, 4, 3, 2, 1, 0.5, or 0.1% on a dry matter basis (wt/wt). In some embodiments, the attractant comprises an amount of particulate additives greater than 90, 85, 80, 80, 75, 70, 65, 60, 55, 50, 45, 40, 35, 30, 25, 20, 15, 10, 5, 4, 3, 2, 1, 0.5, or 0.1% on a dry matter basis (wt/wt). In some embodiments, the attractant comprises an amount of particulate additives greater than 10, 5, 4, 3, 2, 1, 0.5, or 0.1% and less than 90, 85, 80, 80, 75, 70, 65, 60, 55, 50, 45, 40, 35, 30, 25, or 20% on a dry matter basis (wt/wt). In some embodiments, the attractant comprises an amount of particulate additives between about 0.001% and about 20% or between about at least less than 10% a dry matter basis (wt/wt). In some application the particle size of the particulate material is greater than 5 millimeters and in some embodiments the particulate material size is less than 5 mm, less than 0.5 mm, less than 100 microns, less than 10 micron less than 1 micron, less than 0.1 micron. In some embodiments, the particle size of the particulate material may range between 0.5 to 100 nm. In some embodiments, the particulate material comprises on nano-particles. In some embodiments, the particulates comprise spherical particles, non-spherical particles, ordered particles, disordered particles, magnetic particles, non-magnetic particles, particles with a magnetic dipole, material or materials, particles with self-assembly capabilities, charged particles, uncharged particles, colored particles, uncolored particles, or combinations thereof.

The attractant can prevent the trapped insects from breeding. In some embodiments, the attractant prevents the laying or hatching of insect eggs. In some embodiments, eggs laid by insects within the device cannot hatch in the presence of the original attractant. In some embodiments, the attractant comprises an insecticide such as a maggocide or larvacide that renders eggs unviable. Alternatively, in some embodiments, the eggs can hatch but maggots are not able to survive in the attractant composition within the device. The attractant can prevent by replication by comprising an amount of a known insecticide. Alternatively, the chemical conditions of the attractant can prevent the replication. In some embodiments, the attractant comprises additives to enhance massive egg laying by the attracted flies and massive fly eggs hatching to form very large maggot colonies.

The attractant composition can be synthesized by combining the attractant precursor composition, one or more dyes, and one or more particulate additives. One or more components of the attractant can be subjected to a processing step prior to, during, or after combining the components together. For example, the attractant precursor can undergo a processing step prior to combining with the dye and particulate additives. In some embodiments, the components are combined together and then subjected to one, two, three, or four processing steps. In some embodiments, one or more components of the attractant are separately subjected to a processing step, the components are combined together, and then the combined components are subjected to one or more processing steps. Non-limiting examples of processing steps include, washing, sterilizing, cutting, chopping, milling, grinding, blending, fermenting, cooking, filtering, adjusting pH, formulating, dehydrating, freeze drying or packaging.

In some embodiments, one or more components of the attractant are subjected to a physical processing step to adjust the particle size of the material. For example, attractant precursor may be chopped in to smaller sizes, ground, or milled to finer particulates or semi-solid. It is desirable that the chopping or milling process be performed at a temperature that does not degrade or destroy the precursor material of interest. In embodiments that feature both a physical processing step and a fermentation step, the physical processing step can occur before, during, or after transferring to the material to a fermentation vessel to ferment one or more attractant components.

One or more components of the attractant or attractant precursor can be sterilized. In some embodiments, the attractant precursor is sterilized. In examples that include fermenting one or more attractant components, it can be advantageous to sterilize biomass prior to the fermentation step. For example, aquatic or terrestrial biomass may be partial or fully sterilized. Some non-limiting examples of sterilization techniques include cooking, boiling, microwaving, subjecting to steam treatment, exposure to hot water, UV exposure, or a combination thereof. In some embodiments, the precursor material may be exposed in hot water for a period less than 20, 19, 18, 17, 16, 15, 14, 13, 12, 11, 10, 9, 8, 7, 6, 5, 4, 3, 2, 1, 0.5, 0.1 minutes. In some embodiments, the precursor material may be exposed to hot water for a period varying between 5 seconds to 60 seconds. In some embodiments, the attractant precursor material can be sterilized prior to a fermentation step. The treated biomass may admixed or infused with ground cephalopod or effluent from a fermented cephalopod. The infected or inoculated biomass may be further applied as the precursor material or as attractant material. Similar treatments can be applied to aquatic biomass, aquatic waste, fish flotsam or and their combinations thereof with terrestrial biomass. In some embodiments, the attractant components that were not subjected to the sterilization step (such as fluorescent agents or dyes) are mixed with the precursor material before the fermentation process. Alternatively, the attractant components that were not subjected to the sterilization step (such as fluorescent agents or dyes) are mixed with the precursor material after the fermentation process.

In some embodiments, one or more components of the attractant precursor composition is fermented in a fermentation vessel. The fermentation vessel may be open, but preferably closed during the fermentation process. The fermentation step may be performed in a pressurized, semi-pressurized, or variable pressure atmosphere. The fermentation may be aerobic, partially aerobic or anaerobic. In one embodiment, the container may be exposed to ambient light or light of known wavelength. The light exposure can occur continuously or at desirable intervals. Alternatively, in some embodiments, photons are excluded form interacting with the contents of the vessel during the fermentation step. The fermentation reaction may occur at a temperature below 100, 95, 90, 85, 80, 75, 70, 65, 60, 55, 50, 45, 40, 35, 30, 25, 20, 15, 10, 5, or 0° C. In some embodiments, the fermentation reaction may occur at a temperature above 100, 95, 90, 85, 80, 75, 70, 65, 60, 55, 50, 45, 40, 35, 30, 25, 20, 15, 10, 5, 0, −5, or −10° C. In some embodiments, the fermentation reaction occurs between the temperatures of −10° C. and 90° C., or between 0° C. and 60° C.

In some embodiments, at least one component of the attractant composition is subjected to an anaerobic fermentation process. The anaerobic fermentation of the one or more components of attractant is performed in the presence of carbon dioxide, inert gases (i.e. nitrogen), or combinations thereof. In some embodiments, yeast may be added to the precursor material before or post fermentation prior to packaging for deployment. Also yeast and dry ice may be combined for the synthesis of the attractant composition from the attractant precursor material or materials. In other applications, carbohydrate or carbohydrate bearing moieties may be added to the precursor material before or post fermentation prior to packaging. In some embodiments, the attractant or the attractant precursor may comprise of water, yeast, carbohydrate or carbohydrate bearing moieties, biomass, urea and urea moieties and dry ice. The source of water may be from well, stream, tap and other sources of water such as deionized water or distilled water. In some applications it may be preferable that the water be de-oxygenated and de-halogenated (free of halogens) prior to use as a precursor material. It is preferable that water is free of contaminants that may degrade the efficiency of the fermentation process. These various precursors may be combined in various combinations thereof. In some embodiments, fermentation can be initiated by addition of a sample of a previously-fermented attractant composition.

The deployed synthesized attractant may contain partially fermented or fully fermented precursor materials solids, liquid, semi-solid and the fermentation process may continue in the field during deployment. In some applications, the unfermented and fermented precursor may be mixed for deployment in the field. The effluent or semi-solid materials or solids from the anaerobic reaction may be collected and used as an attractant by itself. In some applications the effluent may be combined with various agents describe in the invention and deployed in trapping container. For example the attractant system may comprise of the fermentation products of marine and fresh water animals, disposed in container.

After the completion of the synthesis of the attractant composition, the attractant can be formulated. Formulation can increase or improve the chemical stability, physical stability, overall effectiveness, duration of effectiveness, appearance, packaged density, shelf life, and/or aroma of the attractant composition. The formulated attractant may be dehydrated or freeze dried to prolong shelf life and later be reconstituted with water and other known materials for field deployment. The pH of the attractant may be controlled and stabilized as needed by known methods (i.e. addition of a pH buffer) to a pH less than 11, 10, 9, 8, 7, 6, 5, 4, or 3. The pH of the attractant may be controlled and stabilized to a pH greater than 10, 9, 8, 7, 6, 5, 4, 3, or 2. In some embodiments, the pH is controlled and stabilized to a pH between 2 and 10.

In some embodiments, the pH is controlled and stabilized to a pH between 5 and 9. In some embodiments, attractant formulation can include the addition of physical components to change the structure, characteristics, color, or appearance of the attractant composition. Non-limiting examples of physical components that can be added to formulate the attractant include carbohydrate or carbohydrate moieties, additional particulate materials, treated saw dust, colloidal materials, clay, clays or combination of various clays, activated and non-activated charcoal, resinous materials such as gums (i.e. guar or xanthan gum). In some embodiments, the attractant formulation step comprises addition of yeast, fluorescent dye, or particulate materials to the attractant composition. In some embodiments, the attractant formulation comprises one or more surfactants. In some embodiments, the attractant formulation comprises up to 5% of a surfactant composition (wt/wt). In some embodiments, the attractant formulation comprises a surfactant composition between about 20 ppm and 5000 ppm. In some embodiments, the surfactant material comprises a biodegradable surfactant.

The insect trap as described herein comprises a container which holds the attractant. In some cases, the trap further comprises one or two additional parts, wherein the additional parts are selected from a lid and a modified cover. The container, optional lid, and modified cover are each described in further detail herein.

A device for the effective suppression of a population of certain insect species can be constructed from a container and the attractant described herein. The container can be an open container or a container with an opening or aperture through which the insects can enter the container. The dimensions of the jar can be important for the effectiveness of the trap. An effective container should be large enough to hold a quantity of attractant compositions sufficient to attract the desired insects, and be large enough to hold the insects to be trapped and killed. Similarly, in some embodiments, an effective container is small enough to be transported and deployed in the area which it is desired to suppress the at least one species of insect.

The container can be configured to be of a certain dimension. In some embodiments, the container has an interior volume of at least 100, 200, 300, 400, 500, 600, 700, 800, 900, 1000, 1500, 2000, 2500, 3000, 4000 or 100000 mL. In some embodiments, the container has an interior volume of less than 60000, 5000, 4000, 3000, 2000, 1000, 900, 800, 700, 600, 500, 400, 300, 200, or 100 mL. In some embodiments, the container has an interior volume between about 100-10000 mL; 200-1500 mL; or 500-1500 mL. In some embodiments, the container is configured to be filled up to at least 5, 10, 15, 20, 25, 30, 35, 40, 45, 50, 55, 60, 65, 70, 75, 80, 85, 90, 95, 97, or 99% of its interior volume with the attractant. In some embodiments, the container is configured to be filled up to less than 5, 10, 15, 20, 25, 30, 35, 40, 45, 50, 55, 60, 65, 70, 75, 80, 85, 90, 95, 97, or 99% of its interior volume with the attractant. In some embodiments, the container is configured to hold at least 100, 200, 300, 400, 500, 600, 700, 800, 900, 1000 or 60000 mL of attractant. In some embodiments, the container is at least 1, 2, 3, 4, 5, 6, 7, 8, 9, 10, 11, 12, 13, 14, 15, 16, 17, 18, 20, 22, 24, 26, 28, 30, 32, 34, 36, 38, or 100 inches tall. In some embodiments, the container is less than 5, 6, 7, 8, 9, 10, 11, 12, 13, 14, 15, 16, 17, 18, 20, 22, 24, 26, 28, 30, 32, 34, 36, 38, 40, 44, 48, 52, 56, or 100 inches tall.

The shape of the container dictates the ratio of the surface area to volume of attractant. In some embodiments, the shape of the container is selected such that the volume of attractant is sufficient to attract enough insects into the container to completely cover the surface of the attractant. This layer of dead insects can form a barrier or seal which can increase in the effectiveness of the attractant. In some embodiments, the container is substantially cylindrical, conical, spherical, cubical, or a right rectangular prism. In some cases, the container is substantially cylindrical. In one embodiment, the container comprises curvilinear profile or shape.

In some embodiments, the body of the container may be coated with infra-red reflecting paint including thermal paint or paints. In some applications portions of the container may be coated with infra-red reflecting paint or paints. The application of infra-red reflecting container or containers for the attractant deployment reduces the evaporation of the attractant and prolongs the longevity of the deployed fly suppression system in the field. In some embodiments, when evaporation of the deployed attractant has occurred, water is added to the attractant to maintain effectiveness. In some embodiments, the active life of the deployed attractant is at least 20, 30, 40 50, 80, 100, 130, 150 or 180 days or more.

In some cases, the upper portion of the body may be opaque or coated with opaque material. In some other embodiments, a fluorescing material may be coated on the body of the container or incorporated into the structure of the said trap container. In one embodiment, a pulsing or non-pulsing light emitting diode (LED) may be deployed in close proximity to deployed fly suppression system. In some applications the wavelength of the LED may be turned in response to the nature of the fly or insect or insects of interest.

In some embodiments, the container is configured such that the majority of insects (of the one or more species to be trapped) that have entered the container do not exit the container. This is advantageous from a pest control perspective because when no insects escape from the attractant container, the incidence of resistance is remote and less likely. In some embodiments, the various insects of interest enter the container and are overwhelmed by the attractant and exhibit no inclination to escape from the container. In some embodiments, the various insects of interest enter the container and are unwilling or unable to find the exit to the container. The attracted insects may die from drowning, starvation, from compounds emanating from the attractant, from unknown causes, or combinations thereof. The container can be configured to create an anaerobic seal. In some embodiments, the attracted flies die and form a layered structure over the attractant. The dead flies structure can form an anaerobic seal and a substrate over the attractant to create a self-propagating anaerobic system. The anaerobic seal or dead fly layer structure can be non-hermetic. For example, materials produced by the anaerobic action in the attractant can diffuse through the dead fly layer (anaerobic seal) or structure into the external ambient environment to attract more flies thereby creating a self-propagating open system. In some embodiments, fluids from the attractant may percolate upward through the anaerobic seal to furnish nutrients and attractants for incoming flies. The layered fly structure may be semi-solid layer. In some embodiments, the attractant fluid wets the flies and prevents their escape. The thickness of the anaerobic seal can increase as more dead flies and accumulate in the layer. In some embodiments, the thickness of the anaerobic seal is at least 3, 4, 5, 6, 7, 8, 9 or more than 10 cm. In some embodiments, the thickness of the anaerobic seal is between about 5 cm and about 100 cm.

In some instances, the container is placed in a hole dug in the ground. In cases wherein the container is placed in a hole dug in the ground, the size of the container is not limited by strength of hanging materials, and the container can be either of the sizes described herein, or of an exceptionally large size. For example, in cases wherein the container is placed in a hole dug in the ground, the container can have an internal volume of at least 5, 6, 7, 8, 9, 10, 15, 20, 25, 30, 35, 40, 45, 50, 55, 60, 65, 70, 75, 80, 90, 100, 110, 120, 130, 14, 150, 200, 250, 300 or 400 Liters. As deployed, insects enter the container via the apertures around the top of the container to feed on the nutrients in the attractant disposed in the attractant container. In some embodiments, the container placed in a hole dug in the ground is a decomposable container. In such embodiments, at least one method is used to affect the sealing of the bottom of the jar to the ground to suppress the escape of flies and leakage of fluids from the attractant from the container bottom. For example, a thin rubber sheet or skirt is adapted around the bottom of the jar and overlaying the ground surface. Soil material is arranged or packed around the bottom of the trap jar and the ground surface to seal the bottom of the jar with respect to the ground.

In some embodiments, the attractant container comprises of a biodegradable material. In some applications the biodegradable container with dead trapped flies may be composted with other biodegradable materials. Also, in some embodiments a biodegradable plastic or fluid proof bag may be disposed inside the attractant container as an insert to contain the attractant. The attracted dead flies in the biodegradable bag can be separated from the supporting container and composted. A replacement bag can be deployed in the attractant container for a fresh attractant deployment.

In some embodiments, the attractant container comprises more than one canopy assemblies or more than one discrete canopy assemblies disposed over the container jar. In some embodiments, the canopy assembly is as labeled in FIG. 6A. The canopy assembly optionally comprises one or more elements selected from group consisting of a trap shade, a canopy, a fly funnel, and entry apertures. In some embodiments, the attractant container is a large volume container (for example, more than 5 liter of attractant). In a device featuring a large volume container, a single canopy assembly containing 1 to 4 apertures can limit the number of flies per unit time accessing the large volume of the attractant beneath the canopy assembly. To increase the efficiency in some such cases, the number of canopy assemblies is scaled to match the volume of the attractant in the container. For example, an attractant container with 5 liters of attractant can comprise 2 or 3 separate canopy assemblies disposed over the attractant, and a 20 liter attractant can comprise 4 to 8 canopy assemblies. The deployment of multiple canopy assemblies or assembled canopies over the attractant jar or container offers each insect more openings and opportunities to reach the attractant beneath. The deployment of multiple assembled canopies per container can increase the flux of the attractant in the area surrounding the trap which can attract more flies to the trap. The upper portion of the trap containing multiple assembled canopies may be attached to the container with one of the mechanisms known in the art. For example, the canopies can be attached with quick release clamps, fastener mechanisms, adjustable fasteners, or movable hooks. It is also preferable that flexible sealant or gasket be incorporated between the container and the dome portion containing the canopies to suppress any egress of attractants from these regions. In some embodiments, the lid of the attractant container may contain multiple apertures for flies to enter the trap. Other devices may be attached to the said apertures. In some embodiments, the arrangement of the apertures in the trap follows a geometric pattern. In some embodiments, at least two assembled canopies are attached to the fly container and fa lamp or light source is also attached the container. A device comprising a large volume container may comprise one or more apertures for removing dead flies after device deployment, by mechanical means, or by vacuum, for example. The evacuated container may be cleansed if desirable before refilling with a fresh attractant.

In some embodiments, the lip or the cover of the container is adapted with two or more apertures. The said apertures can communicate between the inside of the container and the outside environment where the pest inhabits. In some embodiments, there is no direct line of sight between the apertures on opposite sides of the lid or cover. The inside portion of the lid may comprise curvilinear features or non-curvilinear structures. The inside of the lid may be adapted with one or more features such as a shaped tubular extension that is conic, convex, concave, or a combination thereof. For example, the lid can have a two shaped tubular extensions, wherein the first is concave, and the second is convex in shape.

In some embodiments, the interior of the lid comprises a coating or a light absorbing material. In some applications, the outer surface of the lid is coated with fluorescing material. For example, at least a portion of the outside surface of the lid can be coated with at least one ultra-violet fluorescing dye, pigment, paint, or combination thereof. In field deployment, insects enter the container via the apertures in the cap to come closer to the attractant disposed in the container. In some embodiments, an insect in the interior of the container cannot have a direct line of site to light outside of the container. In some cases, an insect in the interior of the container cannot see light from outside the top portion of the container and the attached lid.

In some embodiments, two or more apertures may be disposed in the upper portions of the container, or the container and the lid. The apertures in the lid and the container may be partially or fully coincident when the lid is attached to the container for deployment. The formulated media is disposed in a container and the lid of the container comprises a modified funnel with or without shaped shaft or apex.

Portions of the inside of the lid comprise a sealing material to prevent materials emanating from the container from leaking from the periphery of the lip. The lid may be attached to the container by known methods. In some embodiments, the lid is screwed to the main body of the container or the lid is fastened to the container with quick release mechanisms.

In some embodiments, the attractant is disposed inside the container and the top of the container is adapted to support one or more filter materials that exclude flies from the attractant. Non-limiting examples of filter materials include porous plastic, cloth, textiles, screens, biomass, or packed particulate matter. Non-limiting examples of particulate materials include clay materials, silicon powder, diatomaceous earth, infra-red absorbing particulates with or without moisture absorbing particulates. Additionally, in some cases, particulate materials can be disposed over the filter material. Compounds emanating from the attractant can diffuse through the support filter to the outside to attract flies. Also, portions of the attractant can be adsorbed on the particulates disposed over the filter. The attracted fly lands on the particulate, ingesting particulates, and rolling all over the materials disposed over the porous surface. The attracted flies may die from the particulate clogging of their respiratory and digestive system. In some embodiments, the particulates or the infrared absorbing particulates may thermally degrade the flies. In some instances, depending on the nature of the particulate media, the attracted flies lay eggs in the dry or moist particulate media. The majority of the laid eggs may die undeveloped and the majority of maggots emanating from the developed laid eggs may die by thermal degradation, or dehydration or from unknown causes. In some embodiment the some of the upper portion of the container or portions of the cap may comprise of infra-red absorbing layer (not shown). The heat absorbing layer raises the local temperature of the coated area and assist in discouraging fly larvae or maggots from escaping from the container. Maggots creeping along the wall of the vessel in regions over the anaerobic seal layer falls back in to seal surface when the contact the relatively hotter portion of the trap coated with infra red absorbing layer. Fly eggs laid in the proximity of the coated area are thermally degraded and do not hatch in to larva. In some embodiments, maggots in the thermal zone die from thermal degradation.

In one embodiment of this invention, the attractant may be deployed in container with modified cover and the various flies of interest enter the container and are overwhelmed by the attractant and exhibit no inclination to escape from the said container. The attracted flies may die from drowning, starvation, or from compounds emanating from the attractant or from unknown causes. Because of the low incidence of flies escaping from the said attractant container, resistance is remote and less likely.

In some cases, an array of insect traps comprising a plurality of insect traps positioned in proximity to each other, is effective for reducing the population of one or more insect species. In some embodiments, the array comprises at least two traps cluster in an area of less than 100 square feet. In some embodiments, said traps are present in an area of less than 50, 30, 20, 10 square feet. In some embodiments, the array comprises at least 3, 4, 5, 6, 7, 8, 9, or 10 insect traps. In some embodiments, the array is capable of suppressing the population of one or more species of insect of an area greater than 0.1, 0.3, 0.5, 0.7, 1.0, 1.5, 2.0, 3.0, 5.0, 7.0 or 10 acres. In some embodiments of the array, the one or more species are selected from the group consisting of black flies, cluster flies, crane flies, deer flies, face flies, flesh flies, green flies, horn flies, horse flies, house flies, sand flies, sparaerocierid flies, yellow flies, western cherry fruit flies, tsetse flies, cecid flies, phorid flies, sciarid flies, stable flies, mites, and gnats. In some embodiments, each insect trap comprises a chemical attractant. In some embodiments, each insect trap comprises a volume of attractant of at least 100, 200, 300, 400, 500, 600, 700, 800, 900, or 1000 mL. In some embodiments, each trap is configured to capture and kill the insect such that the killed insect is deposited above or with the insect attractant layer. In some embodiments, each insect trap is a device described herein.

In some embodiments, when the deployed container is deemed sufficiently filled, the flies are removed from the container. In some embodiments, when the deployed container is deemed sufficiently filled, the flies are removed from the container by separating the top jar from the attractant container. Alternatively, for large industrial applications, the container may be adapted with one or more apertures for evacuating the dead flies by means of vacuum and refilling the container with a fresh attractant. The deployed attractant container in the cavity can be deemed sufficiently filled with dead flies when at least 60, 65, 70, 75, 80, 85 or 90% of the volume of the container is full of dead flies. In some cases, the container comprises an attractant container and a separate top jar that holds at least a portion of the dead flies. The dead flies may be buried, recycled or composted as seen fit. In some embodiments, the container and the transparent jar may be deployed on the ground and when the insides container is sufficiently filled with dead flies, the covering jar may be separated and the dead flies are buried and disposed of according to local ordinance.

Depending on attractant formulation, the trapped flies may lay copious amount of eggs. The laid eggs die undeveloped and any maggot or maggots emanating from the developed laid eggs die by thermal degradation, or dehydration as moisture in the sludge in the open dishes evaporates. The dead flies mass may be composted and in some applications the content of the dishes may be treated with small amount of bleach prior to disposal according to local ordinance.

In one disposition of this invention to rapidly suppress flies in a given area, effluent or semi-solid or attractant of this invention may be formulated for example with colloidal materials to form an emulsion or semi-solid (solid-liquid) media. The formulated media is disposed in a decomposable trap dish or trap container and placed in a dug hole in the ground. The attracted flies roll and swim in the emulsion in the container and die. The dead flies are buried by covering the dug hole with soil materials. In some instances small amount of ammonium nitrate or may be added to the dead fly sludge before burial.

EXAMPLES

Example 1

A series of 20 liter batches of attractants were prepared by mixing 0.1 to 10 kg of processed aquatic biomass and a quantity of water to reach 20 liters total volume. In some of the mixtures, dry ice (0.1 to 2 kg), yeast (0 to 1 kg), and sugar (0 to 1 kg) were added and the mixture underwent an anaerobic fermentation reaction. Finally, dye (0 or 5 ppm to 1000 ppm) and particulate matter such as clay (0 to 500 g) were added to some of the mixtures.

Example 2

A particular batch of attractant from Example 1 is made by mixing 4.0 kg processed aquatic biomass (processed by blending in a blender) and purified, de-halogenated water (19 liter). The material is cooled to room temperature, and then yeast (100 g) and sugar (100 g) are added. The material is placed in a large container and portions of dry ice are slowly added until the full amount dry ice is added (2 kg) without lowering the temperature of the overall mixture below 20° C. The mixture is allowed to bubble with $CO_2$ gas to remove oxygen from the system. After the attractant mixture stops bubbling, the container is sealed and the mixture undergoes an anaerobic fermentation reaction at 35° C. for 2 days. The mixture is cooled to room temperature, and clay (1 teaspoon), and 2 drops dye are added (AutoPro 375 Antifreeze/Coolant UV Dye 1; supplied by IDQ Corporation—2901 West Kingsley Road, Gartland Tex. 75041).

Example 3

A fly trap lid according to FIG. 1 was constructed. The exterior surface of the canopy was painted with thermal paint. The aperture of fly entrance was constructed to be convex/concave, and the lid was configured to be attached to the container via screw thread.

Example 4

Figure 3:
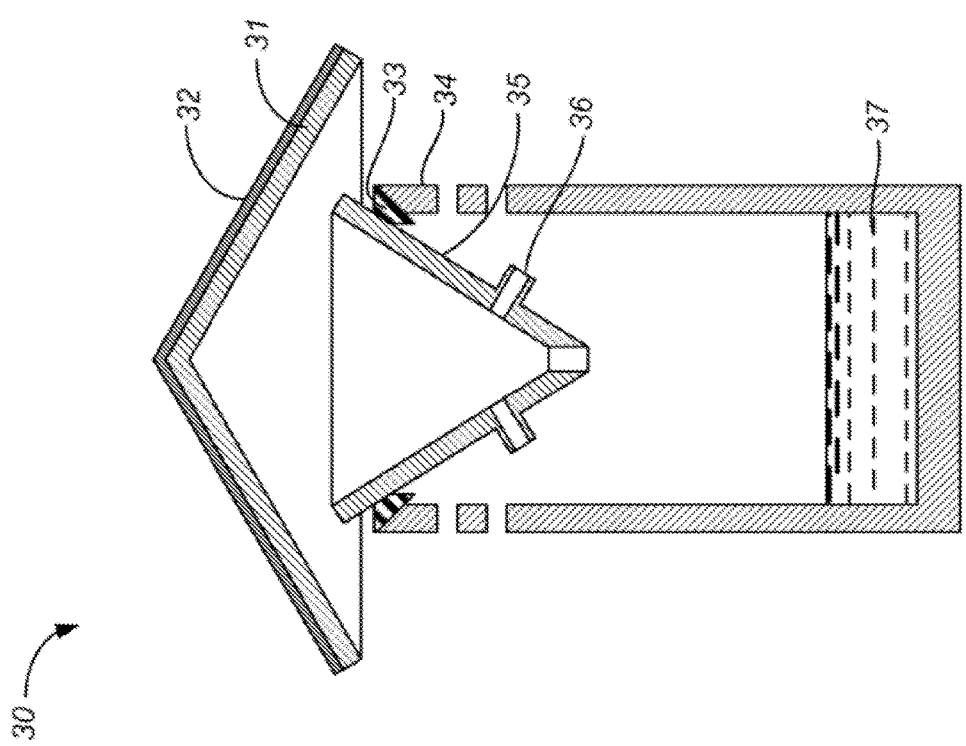
FIG. 3 depicts a fly trap with orifices at the top region of the container.

Insect traps were constructed according to FIG. 2 and FIG. 3. The exterior of the canopy was painted with thermal paint to form a trap shade. A jar (4 L) was used as the container and filled with the attractant of Example 2. The lid was a modified tunnel featuring two apertures for fly entrance. One of the insect traps had additional orifices for small insects on the exterior wall of the container according to FIG. 3. The other insect trap did not have such orifices according to FIG. 2.

Example 5

Figure 4A:
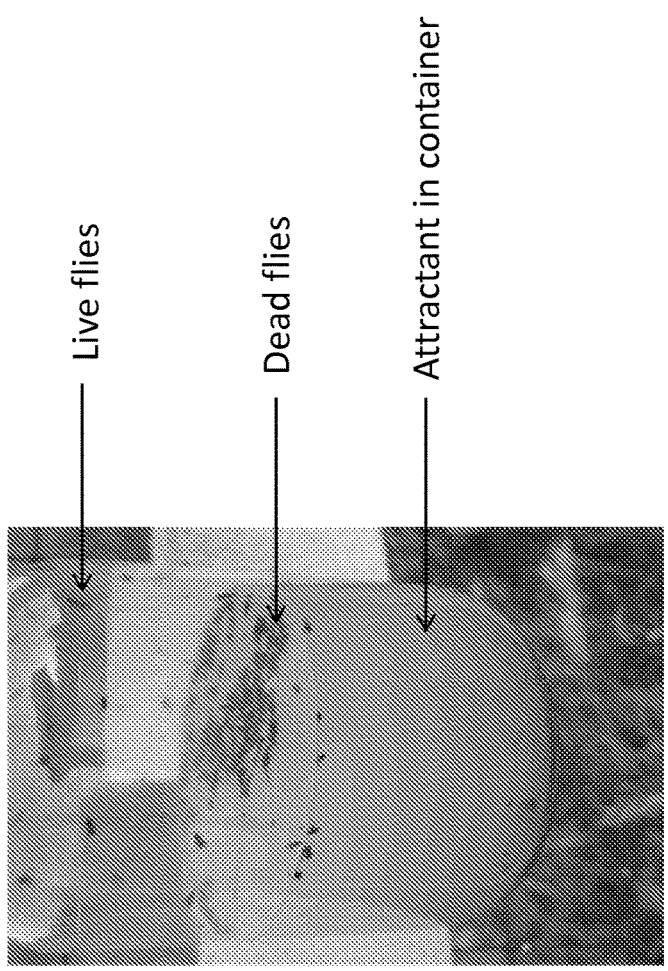
FIG. 4A depicts attractant device 60 minutes after deployment.
Figure 4B:
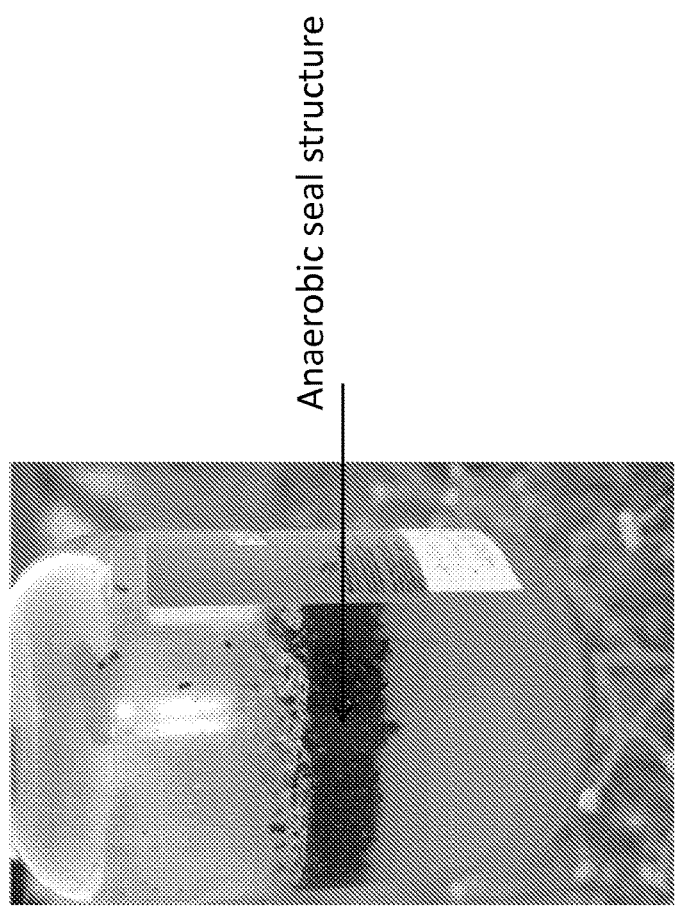
FIG. 4B depicts attractant device 3 days after deployment.
Figure 4C:
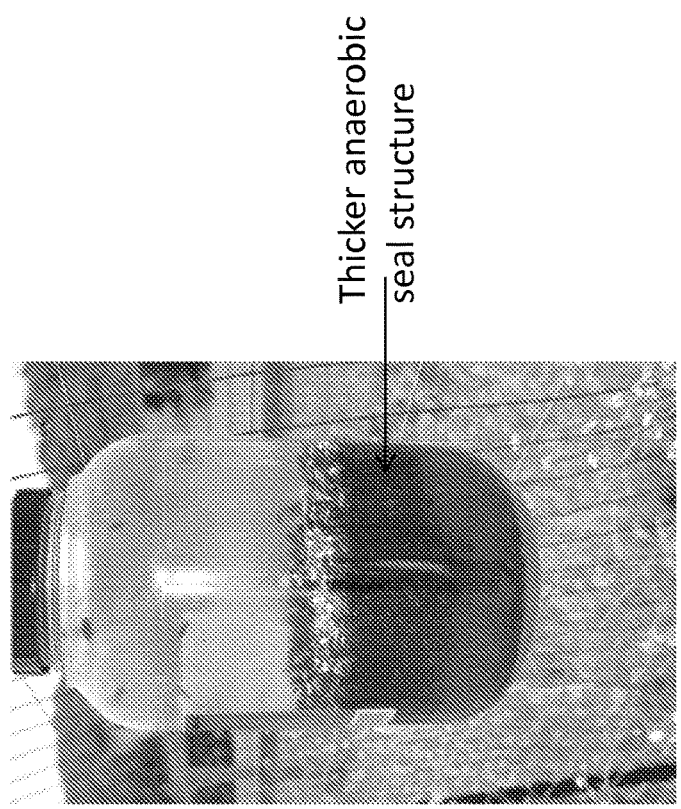
FIG. 4C depicts attractant device 6 days after deployment.
Figure 5:
FIG. 5 depicts the device after deployment and demonstrates a range of varieties of trapped dead flies species, including males and females

A trap comprising an attractant of the invention was deployed in an outdoor setting that was in direct sunlight as shown in FIG. 4A an FIG. 4B. The fly trap was photographed 60 min after deployment as shown in FIG. 4A. Dead flies begin to cover the top of the attractant and live flies remain in the container. The fly trap was photographed 3 days after deployment as shown in FIG. 4B. At this time point, the large number of dead flies form a thick layer on top of the attractant. This layer formed an anaerobic seal structure. The fly trap was photographed 6 days after deployment as shown in FIG. 4C. At this time point, the large number of dead flies formed a very thick layer on top of the attractant which was an anaerobic seal structure. A close up of the deployed (nearly full) trap is depicted in FIG. 5. This shows the large number of trapped dead flies and the relatively low amount of visually apparent maggots in the mixture.

Example 6

Figure 6A:
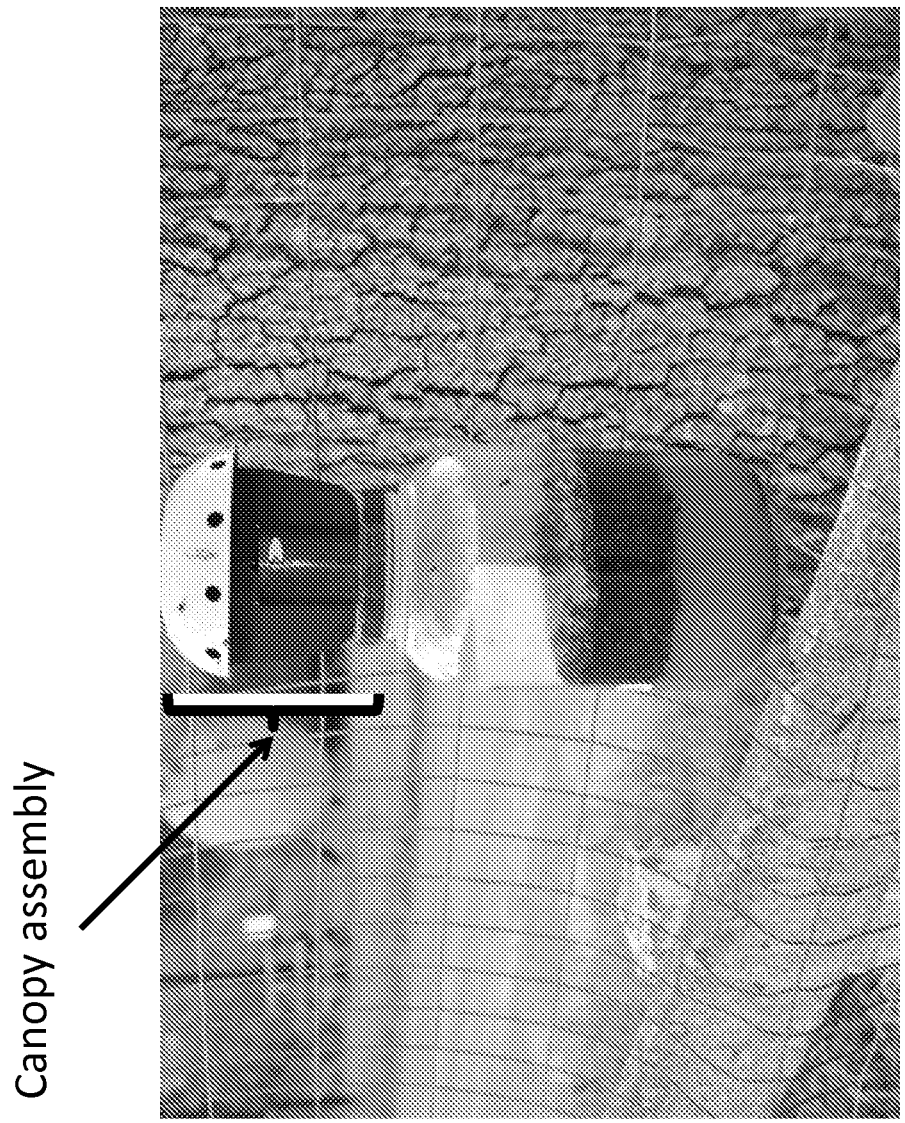
FIG. 6A depicts field deployment of an embodiment of the device in a shade.
Figure 6B:
FIG. 6B depicts a magnified view of the deployed device with container filled with flies.
Figure 7:
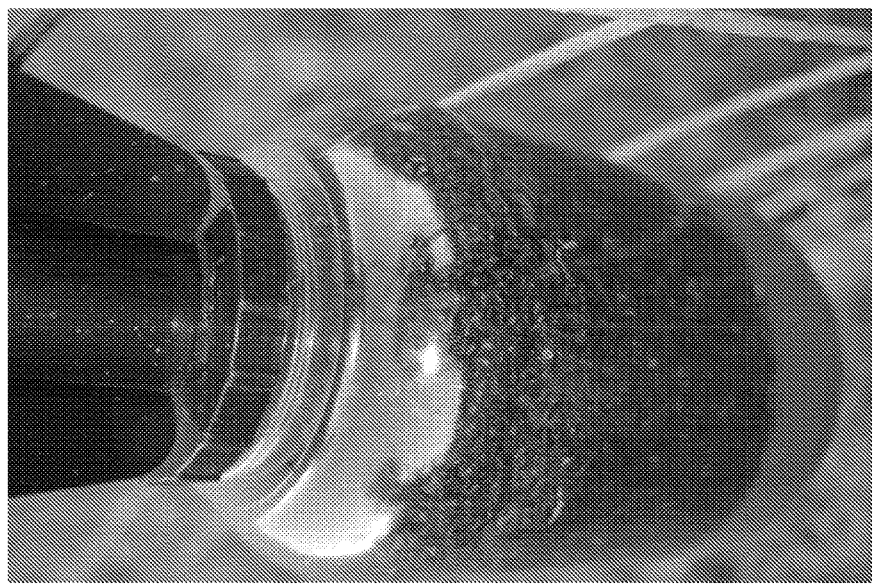
FIG. 7 depicts an embodiment of the device with very thick anaerobic seal structure.

The experiment of example of 5 was repeated, however the insect trap was deployed in an outdoor setting that was in the shade. A photograph of the deployed trap is shown in FIG. 6A and a close-up photograph of trapped flies is shown in FIG. 6B and FIG. 7.

Example 7

Figure 8A:
FIG. 8A horses in a stressed state due to fly induced stress in the absence of device deployment.
Figure 8B:
FIG. 8B depicts happy horses after the calming effects of device deployment draw flies away from the horses.

Horses were photographed on a horse farm that does not contain any insect traps disclosed herein and the photograph is shown in FIG. 8A. The horses are stressed and spending energy to swat and react to flies in the environment. Several days after deployment of the insect traps described herein on the horse farm, a horse was photographed and the photograph is shown in FIG. 8B. The horse now lacks the visually apparent elevated stress level and is not shown spending energy to react to flies in the environment. This result can be considered confirmation that the population of local flies has subsided after the deployment of the insect traps described herein.

Example 8

Figure 9A:
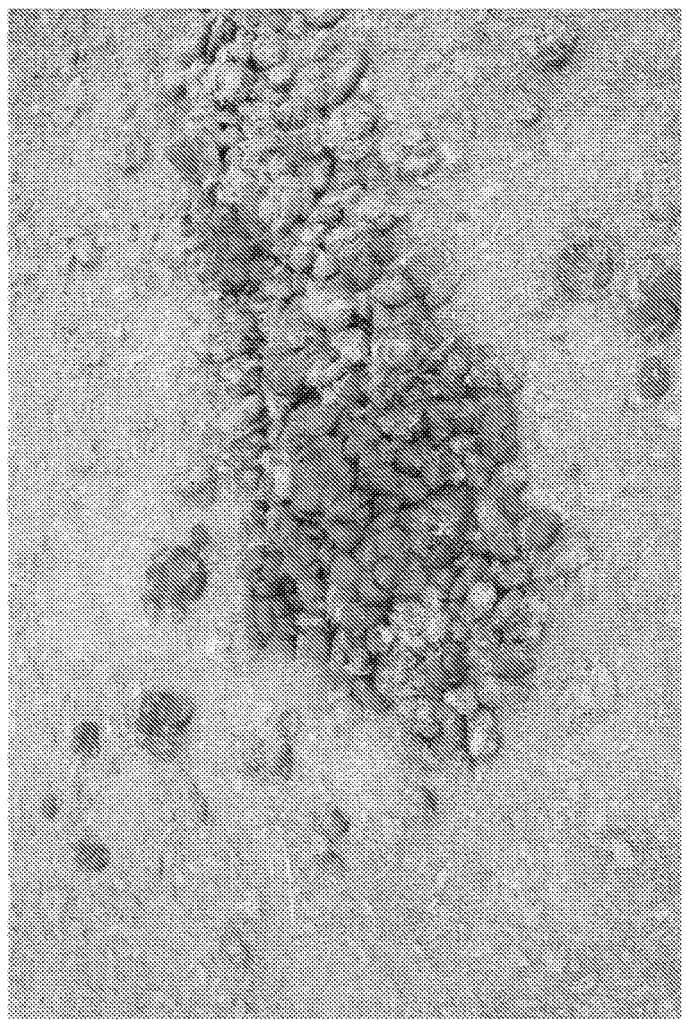
FIG. 9A depicts normal fresh and dried horse manure without maggots and flies in the presence of device deployment.
Figure 9B:
FIG. 9B shows dried manure that does not show signs of maggots and flies in a field indicating the deployment of devices has effectively attracted flies away from manure.

Horses manure was photographed on a horse farm that does contain insect traps disclosed herein and the photograph is shown in FIG. 9A. The fresh and dry manure does not contain maggots or horse flies. Also, the horse manure maintains the original shape and disposition on the ground because the manure was not scattered by birds scavenging for maggots in the manure. This is indicative of a very effective large local fly population suppression in the environment. Several days after deployment of the insect traps described herein on the horse farm, horse manure was photographed and the photograph is shown in FIG. 9B. The manure now lacks the visually apparent divots from the maggots that would be indicative of a large fly population in the environment. The dried horse manure retained its original shape, profile and disposition because it was not contaminated by flies, maggots and not affected by other wild birds scavenging for food. This result can be considered confirmation that the population of local flies has subsided after the deployment of the insect traps described herein.

Example 9

Figure 10:
FIG. 10 is an enlarged view of disposed dead trapped flies being used for animal recycling.
Figure 11:
FIG. 11 depicts dead flies of FIG. 10 in open space and being eaten by other organisms.

The contents of the insect trap of example 5 were examined 6 days after deployment. The mixture of attractant solution and flies was emptied onto the soil to be used as fertilizer and food for other animals. Photographs of the fertilizer on the ground are shown in FIG. 10 and FIG. 11.

Example 10

Figure 12:
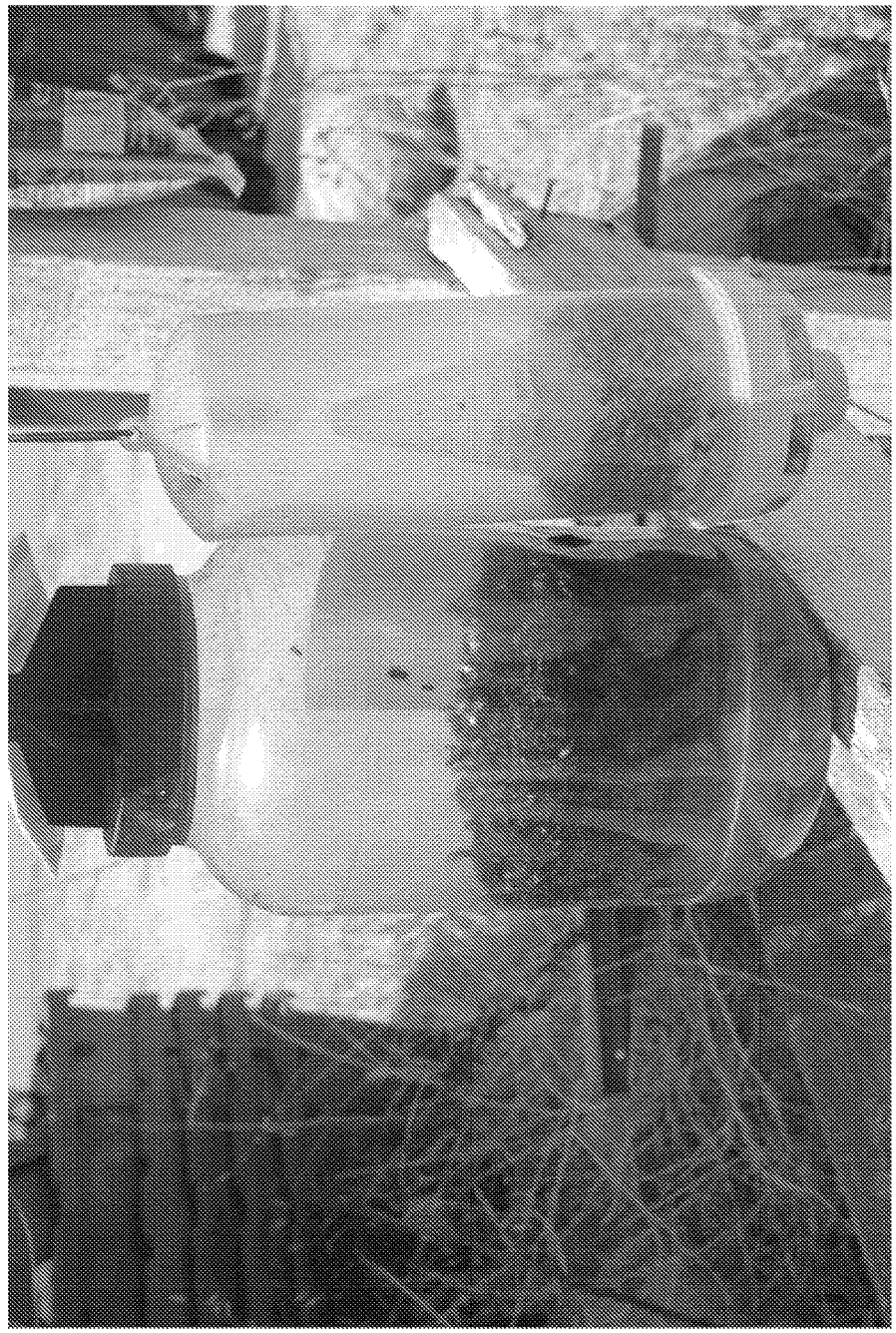
FIG. 12 shows species selectivity of the device as the device is deployed in proximity to a yellow jacket trapping device.

An insect trap as disclosed herein was deployed in an outdoor environment directly next to a commercially available wasp trap. Six days after deployment, the two traps were examined and photographed (FIG. 12). The insect trap as disclosed herein trapped primarily flies and did not trap a visually apparent number of wasps. This result indicated the species selectivity of the insect trap as disclosed herein.

Example 11

Figure 13B:
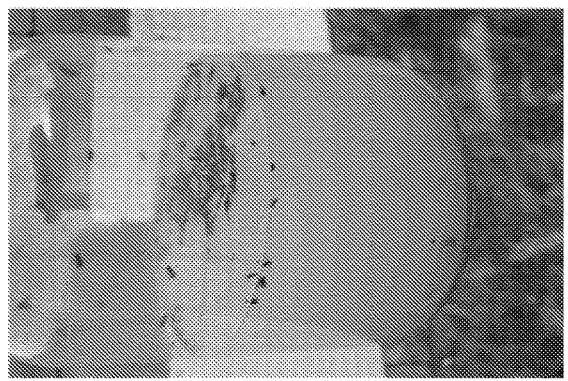
FIG. 13B shows a fly trap device comprising attractant composition A and further comprising hydrophilic dye A, 60 minutes after deployment.
Figure 13A:
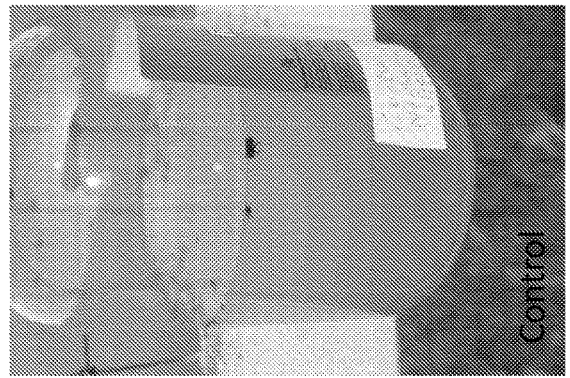
FIG. 13A shows a fly trap device containing attractant composition A, 60 minutes after deployment.
Figures 14A, 14B:
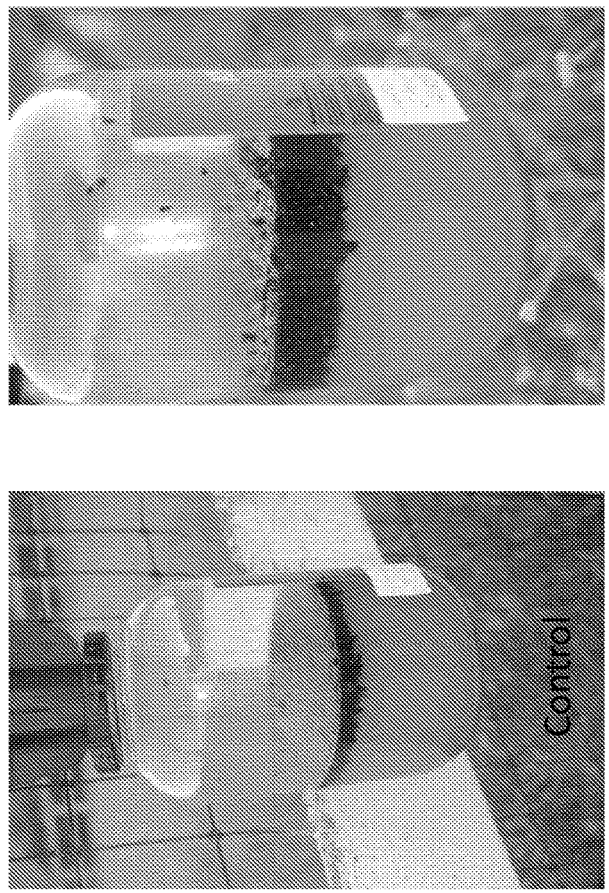
FIG. 14A shows a fly trap device containing attractant composition A, 3 days after deployment.
FIG. 14B shows a fly trap device comprising attractant composition A and further comprising hydrophilic dye A, 3 days after deployment.
Figure 15C:
FIG. 15C shows a fly trap device comprising attractant C (water) as a control.
Figures 15A, 15B:
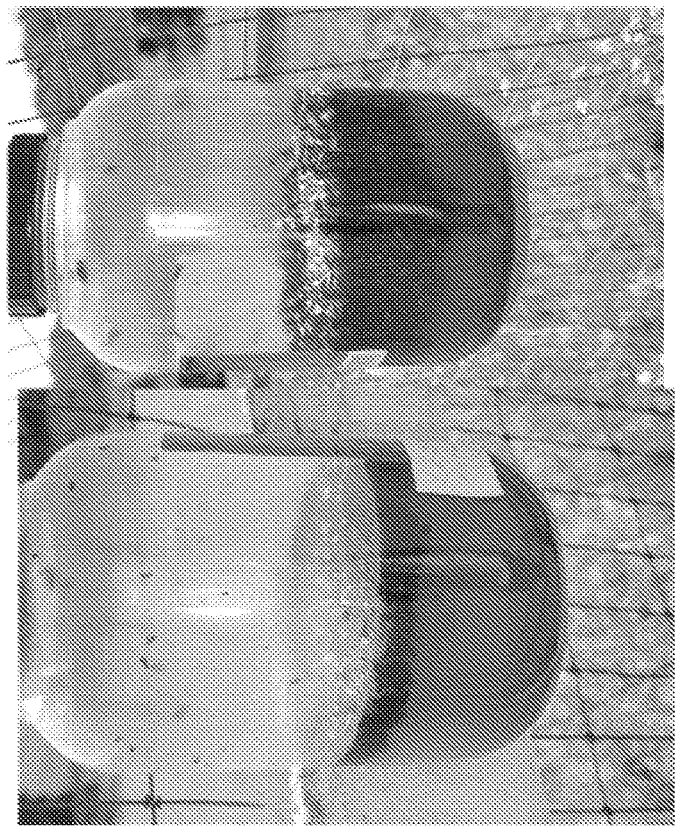
FIG. 15A shows a fly trap device containing attractant composition A, 6 days after deployment.
FIG. 15B shows a fly trap device comprising attractant composition A and further comprising hydrophilic dye A, 6 days after deployment.

Four different attractant compositions (A, B, and C) were placed in identical container/lid insect trap devices disclosed herein, and the traps were deployed in an outdoor environment as an experiment to test the efficacy of the attractant compositions. The insect trap device containing attractant composition A is shown at three different time points in FIG. 13A, 14A, 15A (60 minutes, 3 days, 6 days respectively after deployment). The insect trap device containing attractant composition B which was the attractant composition A and further comprising dye A is shown at three different time points in FIG. 13B, 14B, 15B (60 minutes, 3 days, 6 days respectively after deployment). The insect trap device containing attractant composition C which was only water and used as control is depicted in FIG. 15C, six days after deployment. As can be seen from the amount of flies trapped in the traps, effluent B was much more effective than control D.

Example 12

Figure 16:
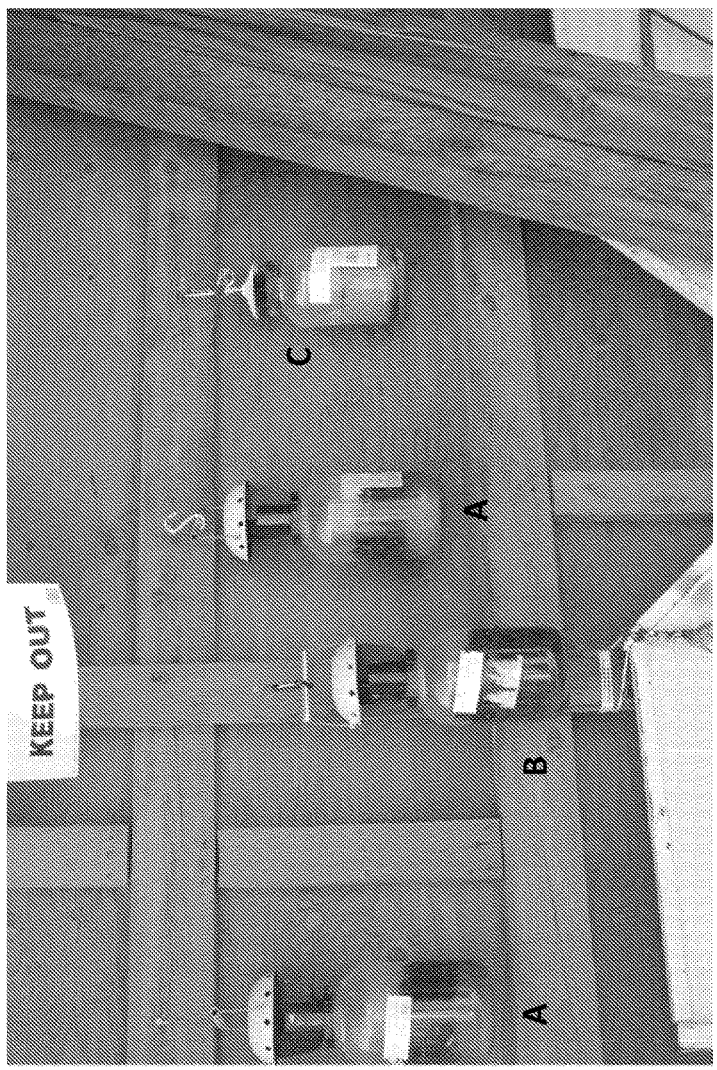
FIG. 16 depicts a set of deployed fly traps (array) with differing attractant compositions.
Figure 17:
FIG. 17 is a close-up of the control fly trap which has water in place of the attractant compositions described herein.

An array of fly traps as described herein was deployed in an outdoor environment in close proximity to one another. The cluster of insect traps were photographed 6 days after deployment and displayed in FIG. 16. The trap labeled A in FIG. 16 was deployed containing an attractant composition comprising ground aquatic biomass. The trap labeled B in FIG. 18 was deployed containing an attractant composition comprising the effluent from the same aquatic biomass without a grinding step. The trap labeled C in FIG. 16 was deployed with an attractant comprising an excess amount of the dye relative to the other deployed traps. The trap in FIG. 17 was deployed containing an attractant composition consisting essentially of water (for a control).

Example 13

Figures 18A, 18B:
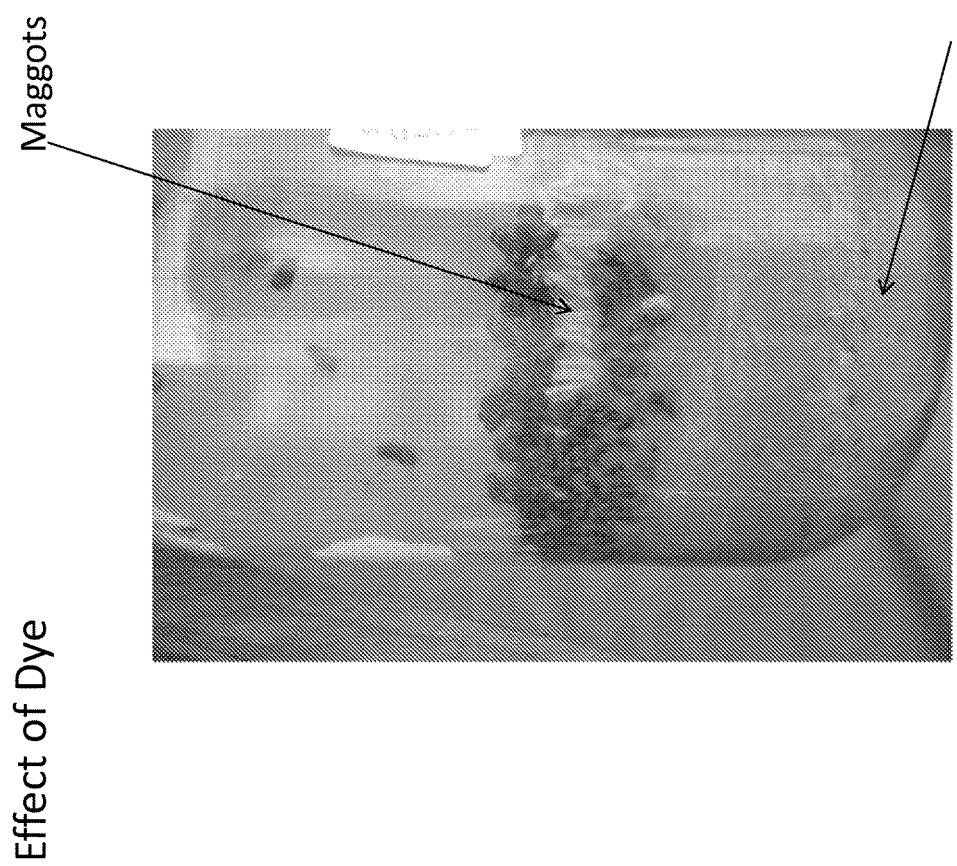
FIG. 18A shows the presence of maggots in a deployed fly trap comprising attractant and lacking a dye.
FIG. 18B shows the absence of maggots in a deployed fly trap comprising attractant comprising a dye.
Figure 19:
FIG. 19 is a Texas longhorn burdened by flies in an area lacking devices and methods described herein.

The fly trap of example 10 (Attractant B) was deployed without dye. The insect trap devices are shown in FIG. 18A, 6 days after deployment, and a population of maggots is visually apparent in the attractant composition.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An insect attractant composition comprising:
    an anaerobically fermented biomass comprising an aquatic biomass;
    a particulate matter; and
    a dye that has an emission wavelength of less than 500 nanometers;
    wherein the composition is a liquid;
    wherein the insect attractant composition selectively attracts at least one insect that is implicated in stressing or transmitting disease to livestock;
    wherein the particulate matter comprises at least one substance selected from the group consisting of ball clay, bentonite clay, polymer clay, Edgar plastic kaolin, a silicon powder, a carbon particulate activated carbon volcanic ash a kaolinitic clay montmorillonite and saw dust.

2. The composition of claim 1, wherein the anaerobically fermented biomass is at least partially sterilized prior to fermentation.

3. The composition of claim 2, wherein the anaerobically fermented biomass is sterilized by at least one sterilization process selected from the list consisting of cooking, boiling, microwaving, subjecting to steam treatment, exposure to hot water, and UV exposure.

4. The composition of claim 1, wherein the anaerobically fermented biomass contacts an anaerobic fermenting microbe during fermentation.

5. The composition of claim 4, wherein the anaerobic fermenting microbe comprises at least a yeast or a fungal agent.

6. The composition of claim 1, wherein the anaerobically fermented biomass is contacted to at least one carbohydrate or a carbohydrate moiety during fermentation.

7. The composition of claim 1, wherein the anaerobically fermented biomass is fermented in an oxygen-excluding environment that comprises carbon dioxide and does not comprise oxygen sufficient to inhibit anaerobic fermentation.

8. The composition of claim 7, wherein the carbon dioxide is introduced to the anaerobically fermented biomass as dry ice.

9. The composition of claim 1, wherein the anaerobically fermented biomass is fermented in an oxygen-excluding environment that comprises an inert gas and does not comprise oxygen sufficient to inhibit anaerobic fermentation.

10. The composition of claim 1, wherein the aquatic biomass is at least one biomass selected from the group consisting of cuttlefish, mussel, octopus, squid, clam, oyster, scallop, snail, slug, aquatic flotsam, fish waste, aquatic biomass effluent and aquatic waste.

11. The composition of claim 1, wherein the anaerobically fermented biomass comprises effluent.

12. The composition of claim 11, wherein the effluent comprises an aquatic biomass effluent.

13. The composition of claim 1, wherein the dye is at least one dye selected from the group consisting of an edible dye, a parenteral dye, a biodegradable dye, and a fluorescent dye.

14. The composition of claim 1, wherein the dye is present at a concentration of from 0.01 ppm to 1000 ppm dye on a dry matter basis (wt/wt).

15. The composition of claim 1, wherein the composition does not comprise an insecticide.

16. The composition of claim 1, wherein the insect that is implicated in stressing or transmitting disease to livestock is at least one insect species of insect selected from the group consisting of a black fly, a cluster fly, a crane fly, a deer fly, a face fly, a flesh fly, a green fly, a horn fly, a horse fly, a house fly, a sand fly, a sparaerocierid fly, a yellow fly, a western cherry fruit fly, a tsetse fly, a cecid fly, a phorid fly, a sciarid fly, a stable fly, a mite, and a gnat.

17. The composition of claim 1, wherein a second insect species is not selectively attracted, and wherein the second insect species is at least one species selected from the group consisting of a grasshopper, a bee and a butterfly.

18. The composition of claim 1, wherein the insect that is implicated in stressing or transmitting disease to livestock is a house fly.

19. The composition of claim 1, wherein the insect that is implicated in stressing or transmitting disease to livestock is a horse fly.

* * * * *